United States Patent [19]

Marshall

[11] 4,023,275

[45] May 17, 1977

[54] MOUNT FOR THE WORKTABLE OF A DENTAL SURVEYOR

[75] Inventor: Kenneth Henry Marshall, Castlecrag, Australia

[73] Assignee: Premach Pty. Limited, Sydney, Australia

[22] Filed: July 22, 1975

[21] Appl. No.: 598,055

[30] Foreign Application Priority Data

Aug. 1, 1974 Australia .......................... 8388/74

[52] U.S. Cl. .................................................. 32/67
[51] Int. Cl.² ......................................... A61C 3/00
[58] Field of Search .................................. 32/67, 32

[56] References Cited

UNITED STATES PATENTS 1,472,034  10/1923  Asquith ................................. 32/67
2,095,665  10/1937  Greth ................................... 32/67

Primary Examiner—Robert Peshock

Attorney, Agent, or Firm—Finnegan, Henderson, Farabow & Garrett

[57] ABSTRACT

A dental surveyor to be used by a mechanic for the preparation of a jig carrying a cutting-bur guide sleeve to assist a dental surgeon in tooth preparation for the anchoring of a bridge, the surveyor comprising a pair of parallel traversing arms carrying a stylus and a sleeve holder, respectively, a worktable on an adjustable universal mount at an upper end of a stem also supported for universal movement in an intermediate clamping housing, and a floor beneath the stem and having two concentric tracks selectively engageable by the end of the stem, the inner track when engaged confining the worktable to rotation about a fixed fulcrum and the outer track when engaged confining the worktable to rotation and swivelling at a predetermined inclination to the axis of the fixed fulcrum, thus enabling the mechanic to vary the axes of the sleeves of successively prepared jigs so that tooth reduction by the surgeon on the patient may be achieved.

3 Claims, 4 Drawing Figures

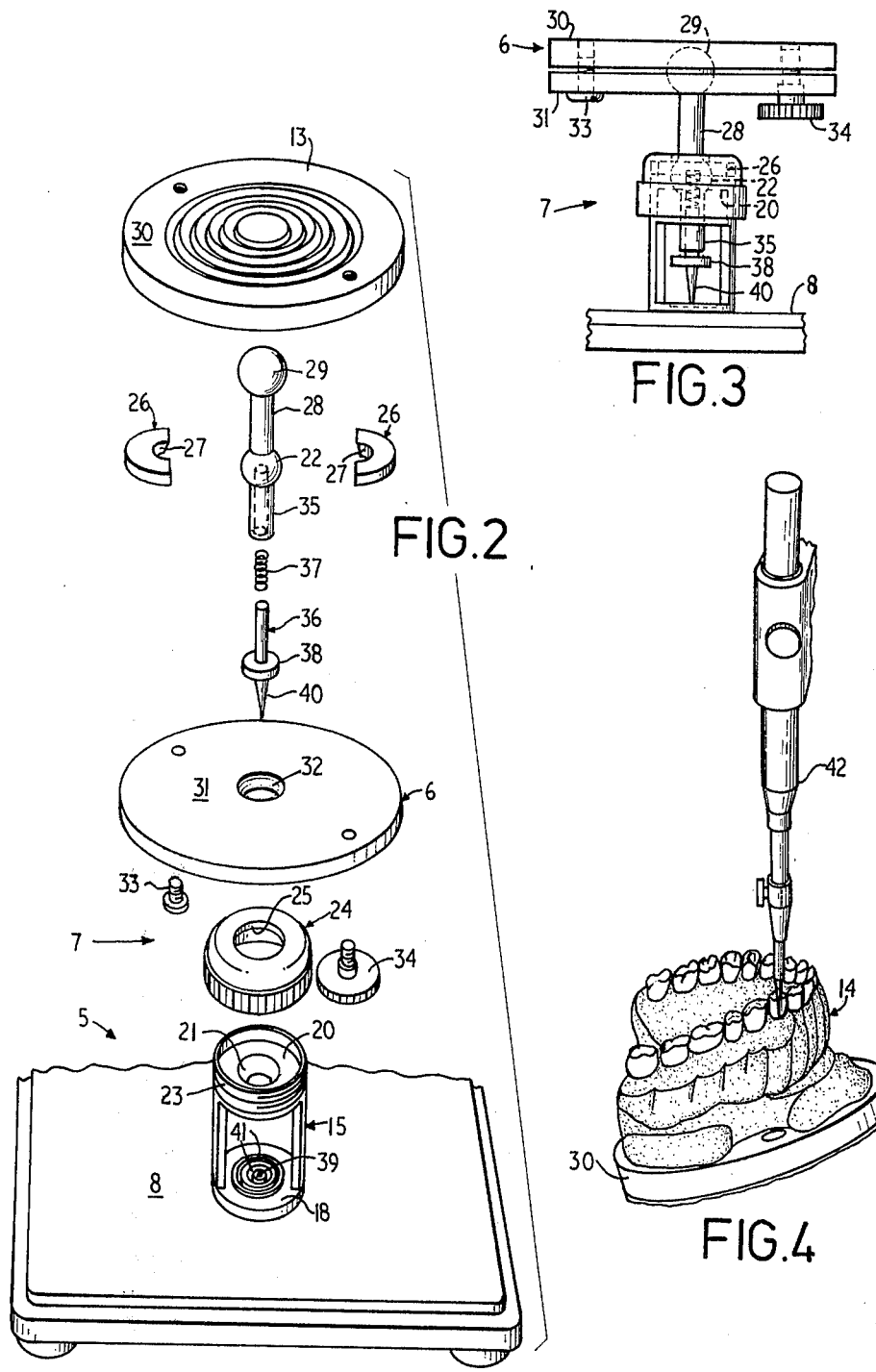

MOUNT FOR THE WORKTABLE OF A DENTAL SURVEYOR

This invention relates to mounts for worktables on dental surveyors.

In dental preparation for bridgework, and the like, two or more teeth of the patient are reduced to a spigot onto which is cemented the anchoring caps of a bridge. For improved adhesion these spigots are frequently conical having a taper of about 3½°. It has been conventional practice prior to this invention for all of the necessary tooth preparation for bridgework anchorage to be done manually by the dental surgeon, requiring a considerable degree of skill. As the teeth in a patient's jaw frequently do not have parallel axes, and undercutting of a tooth from the axis of the path of insertion of the intended bridge cannot be tolerated, it sometimes occurs that patients are advised against the fitting of a bridge because of the excessive reduction necessary in an area of a tooth, to a stage where the pulp becomes damaged.

More recently surgeons have been assisted by the advent of paralleling device secured to the patient's jaw, while more recently still a preformed jig for guiding the bur, constructed upon a model of the patient's teeth, has been prepared by a mechanic and supplied to the surgeon. This jig, to be gripped between the patient's jaws, has included a guide sleeve to accommodate rotatably a housing for a cutting bur. Such a jig is the subject of U.S. Pat. No. 3,600,810 filed Aug. 24, 1971 and assigned to the present assignee. In the instance of both the above device and jig, although the actual reduction by cutting of the teeth is performed conically, axes of the individual anchoring teeth for each bridge have hitherto been parallel. This has limited the use of such aids to patients with reasonably uniform teeth formation.

It is the principal object of this invention to provide in a dental surveyor a form of mount for the worktable which will enable its rotatable axis to be varied within controlled limits to permit a dental jig, for utilization by a dental surgeon to control the reduction of teeth for anchoring spigots in bridgework, to be produced whereby the axes of these spigots vary from parallel alignment within predetermined limits.

According to one feature of the invention there is provided a dental surveyor for use in the construction of a dental aid jig incorporating a guide sleeve for a cutting bur, and comprising a worktable for mounting a dental model, a rotatable mount for the worktable including an adjustable ball and socket support, a telescopic stem depending from said support, a floor beneath said stem provided with two concentric tracks the inner one of which is a fixed fulcrum means, an end portion on the telescopic stem selectively engageable with said tracks, a supporting pillar, two articulated traversing arms mounted upon said pillar and carrying, respectively, and in parallel alignment a stylus and a holder for the sleeve of said dental jig, spring means tending to retain the end portion of said stem in its selected track, an intermediate ball on said stem, and an adjustable clamping housing supporting said intermediate ball and when clamped on said intermediate ball securing said stem against rotation and swivelling, whereby the mean occlusal plane of said worktable is set and secured by relating said stylus to the teeth on said dental model while rotation of said worktable is confined about a fixed fulcrum through register of the end portion of said stem in the inner one of said tracks, and the relative position of said sleeve supported by said holder is set and secured by setting of said worktable at a selected swivelled position while the end portion of said stem is engaged in the outer one of said tracks.

A preferred form of the invention is illustrated in the accompanying drawings, in which:

FIG. 2 is an exploded perspective view of the component parts of the axially displaceable mount only;

FIG. 3 is fragmentary elevation of the assembled mount; and

FIG. 4 is a fragmentary perspective view of the cast secured to the mount showing the operation of determining, by the use of an overhead component on the surveyor, the worktable fulcrum by comparison of the axes of anchoring teeth for intended dental bridgework.

Figure 1:
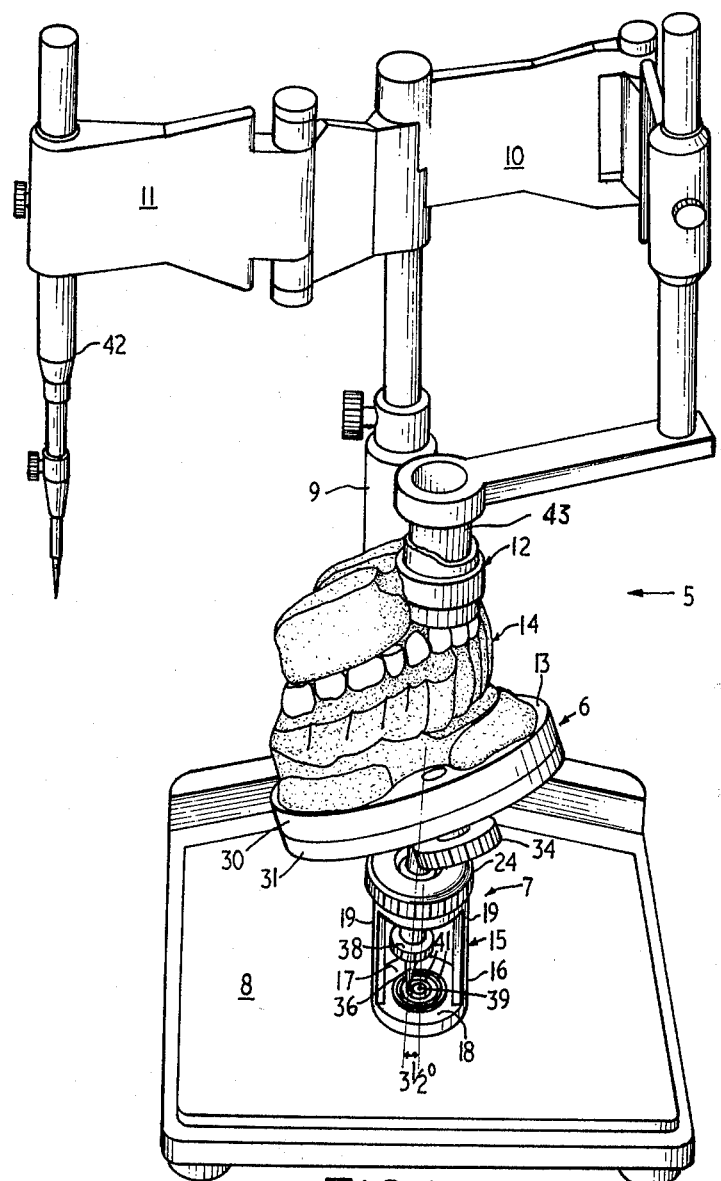
FIG. 1 is a perspective of the dental surveyor showing a jig and cast in place.

The preferred embodiment of the invention shown in the drawings will now be described in which a dental surveyor 5 incorporates a rotatable worktable 6 provided with a mount 7 of the invention. The surveyor has a base platform 8 to which is affixed the said mount 7 with a pillar 9 supporting articulated arms 10 & 11 for the support of components for preparing a dental jig 12. The worktable 6 has an upper surface 13 for the support through a mounting wad of a dental cast 14 to which it is intended that the jig 12 be attachable.

The worktable mount 7 preferably comprises a hollow cylindrical housing 15 closed at its lower end 16 by a case hardened metal floor 18 on the base platform 8 and having opening 17 in its wall to form wall portions 19. The housing 15 contains a medial bush 20 with an inverted conical bore 21 into which is swivelably located a ball 22. The outer wall of the housing is threaded at 23 to accept an internally threaded cap 24 with a bored upper end 25 which houses a split bearing 26 with a conical bore 27 so that tightening of the cap 24 upon the housing 15 clamps the ball 22 tightly between the bush 20 and the bearing 26 to secure the worktable 6 against rotation and swivelling.

An integral stem 28 extends upwardly from the ball 22 and is surmounted by a second ball 29. The worktable 6 is in two parts 30 & 31 provided with part spherical bores as shown at 32. The parts 30 & 31 are clamped about the ball 29 by an anchor screw 33 and a clamping thumb screw 34. The worktable 6, therefore, can rotate and swivel about the ball 29 on the fulcrum of the stem 28, and the fulcrum of the latter can swivel about the ball 22.

A downwardly extending and integral stem 35 is provided on the ball 22 which protrudes through the bore in the bush 20. The stem 35 consists of an upper tubular portion and a lower telescoping portion in the form of a pointed pin 36 slidable within the upper tube 35. A helical spring 37 is accommodated within the tubular portion 35 outwardly to telescope the stem. A flanged collar 38 fixed near the lower end of the pin permits gripping by an operator to displace the pin 38 against the action of the spring 37.

The case hardened floor 18 of the mount 7 is provided with a cavity 39 near its centre which will function as a fixed fulcrum track engaged by the point 40 of the pin 36 which is maintained therein by the helical spring 37. Preferably, the stem point 40 which is perpendicular to the base platform 8 when engaging in the fixed fulcrum track 39, will permit the worktable to rotate while preventing swivelling. A circular track 41, in the form of a groove, surrounds the fulcrum 39 in the floor and is of a predetermined diameter. Alternatively, several concentric tracks 41 may be provided. Manual retraction of the pin 36 against spring tension will enable the pin point 40 to be withdrawn from the fulcrum 39 whereby upon the displacement of the worktable it may be re-engaged with a selected track 41 in the floor 18. Where the intended degree of taper on the tooth spigot is say 3½°, the diameter of one of the tracks 41 will be so arranged that the fulcrum of the worktable 6 may be swivelled in an orbit at any part of which it is displaced from an upright axis, i.e. from the fixed fulcrum, by a constant angle, say 3½° or slightly less. The diameter of the other tracks 41 may correspond to axis inclinations of say 2° and 4° for those instance, where a different degree of taper is required.

It will be seen, therefore, that a cast 14 affixed to the upper surface 30 of the worktable 6 may be swivelled if the clamping screw 34 is loosened so that a stylus 42 can be aligned with a selected tooth in the cast 14 shown by FIG. 4 for determination of the necessary degree of axis inclination. In any position of the table 6 the greatest angular difference between any pair of axes, relative to respective teeth, will be 3½° should the corresponding track 41 be engaged by the stem point 40. In this way maximum tooth structure may be utilised in bridgework preparation even though the anchoring points thereof are teeth with considerably different axes.

The articulated arm 11 of the surveyor 5 is provided with the vertically displaceable stylus 42 which can be positioned in front of a selected tooth as shown in FIG. 4 to determine the disposition of tooth material about the axis of said tooth. The other articulated arm 10 carries a sleeve 43 for accepting and positioning the jig 12, which sleeve will also have an axis parallel to the axis of the stylus 42. Formation of the jig 12 in a conventional manner may then proceed.

Whereas a preferred embodiment has been described in the foregoing passage it should be understood that other forms are possible within the scope of the invention. Many other applications for a surveyor incorporating the invention will be found, for example it may be used to advantage for surveying for clasping in the fabrication of partial dentures to indicate upon individual teeth of a model, or cast, of a dental patient the desired amount of undercut for retention of the denture.

What I claim is:

1. A dental surveyor for use in the construction of a dental aid jig incorporating a guide sleeve for a cutting bur, and comprising a worktable for mounting a dental model, a rotatable mount for the worktable including an adjustable ball and socket support, a telescopic stem depending from said support, a floor beneath said stem provided with two concentric tracks the inner one of which is a fixed fulcrum means, an end portion on the telescopic stem selectively engageable with said tracks, a supporting pillar, two articulated traversing arms mounted upon said pillar and carrying, respectively, and in parallel alignment a stylus and a holder for the sleeve of said dental jig, spring means tending to retain the end portion of said stem in its selected track, an intermediate ball on said stem, and an adjustable clamping housing supporting said intermediate ball and when clamped on said intermediate ball securing said stem against rotation and swivelling, whereby the mean occlusal plane of said worktable is set and secured by relating said stylus to the teeth on said dental model while rotation of said worktable is confined about a fixed fulcrum through register of the end portion of said stem in the inner one of said tracks, and the relative position of said sleeve supported by said holder is set and secured by setting of said worktable at a selected swivelled position while the end portion of said stem is engaged in the outer one of said tracks.

2. A dental surveyor as claimed in claim 1, wherein said outer track is a circular groove of a diameter so as to permit said worktable to swivel at a uniform inclination to the axis of said fixed fulcrum of substantially 3½°.

3. A dental surveyor as claimed in claim 1, further comprising a base plate on which said floor and said supporting pillar and said clamping housing are mounted, said worktable being supported by said clamping housing.

* * * * *